(12) United States Patent
Mobbs et al.

(10) Patent No.: US 12,102,425 B2
(45) Date of Patent: *Oct. 1, 2024

(54) SYSTEM AND METHODS FOR MONITORING THE SPINE, BALANCE, GAIT, OR POSTURE OF A PATIENT

(71) Applicant: TRACPATCH HEALTH, LLC, Wyoming, MI (US)

(72) Inventors: Ralph J. Mobbs, Clovelly (AU); Curt Wiedenhoefer, Davis, CA (US); Graeme Phillip McMeekan, Naples, FL (US); Anthony J. Habib, Sacramento, CA (US)

(73) Assignee: TRACPATCH HEALTH, LLC, Wyoming, MI (US)

( * ) Notice: Subject to any disclaimer, the term of this patent is extended or adjusted under 35 U.S.C. 154(b) by 909 days.

This patent is subject to a terminal disclaimer.

(21) Appl. No.: 17/121,309

(22) Filed: Dec. 14, 2020

(65) Prior Publication Data

US 2021/0228111 A1   Jul. 29, 2021

Related U.S. Application Data

(63) Continuation of application No. 16/775,026, filed on Jan. 28, 2020, now Pat. No. 10,863,928.

(51) Int. Cl.
*A61B 5/00* (2006.01)
*A61B 5/11* (2006.01)

(52) U.S. Cl.
CPC .......... *A61B 5/1117* (2013.01); *A61B 5/0004* (2013.01); *A61B 5/112* (2013.01);
(Continued)

(58) Field of Classification Search
CPC . A61B 5/0004; A61B 5/02438; A61B 5/1116; A61B 5/1117; A61B 5/112;
(Continued)

(56) References Cited

U.S. PATENT DOCUMENTS

| 3,724,651 A | 4/1973 | Link |
| 4,353,135 A | 10/1982 | Forte et al. |

(Continued)

FOREIGN PATENT DOCUMENTS

| CN | 201537084 | 8/2010 |
| CN | 102472719 | 5/2012 |

(Continued)

OTHER PUBLICATIONS

Official Communication for U.S. Appl. No. 15/077,793 mailed Aug. 24, 2022.

(Continued)

*Primary Examiner* — May A Abouelela
(74) *Attorney, Agent, or Firm* — Branch Partners PLLC; Bruce E. Black

(57) ABSTRACT

A system for monitoring a user that includes a sensor unit configured and arranged to be disposed on the user, the sensor unit including an accelerometer and a communication arrangement; and at least one processor configured and arranged for performing actions including: receiving signals from the accelerometer of the sensor unit; determining a step count from the signals; determining a gait velocity from the signals; determining a step distance from the signals; determining a posture of the user from the signals; and determining a gait posture index as a function of the step count, gait velocity, step distance, and posture. In other embodiments, the system can be used to determine metrics other than the gait posture index, such as a fall prediction score based on gait velocity and posture deviation.

20 Claims, 9 Drawing Sheets

(52) U.S. Cl.
CPC ............ *A61B 5/486* (2013.01); *A61B 5/6833* (2013.01); *A61B 5/7278* (2013.01); *A61B 5/7282* (2013.01); *A61B 5/742* (2013.01); *A61B 2562/0219* (2013.01)

(58) Field of Classification Search
CPC ..... A61B 5/486; A61B 5/6832; A61B 5/6833; A61B 5/7278; A61B 5/7282; A61B 5/742; A61B 2562/0219
See application file for complete search history.

(56) References Cited

U.S. PATENT DOCUMENTS

| | | |
|---|---|---|
| 4,756,312 A | 7/1988 | Epley |
| 5,833,603 A | 11/1998 | Kovacs et al. |
| 6,588,931 B2 | 7/2003 | Betzner et al. |
| 8,784,274 B1 | 7/2014 | Chuang |
| 8,990,041 B2 | 3/2015 | Grabiner et al. |
| 9,138,174 B2 | 9/2015 | Jin et al. |
| 9,176,932 B2 | 11/2015 | Baggen et al. |
| 10,182,746 B1* | 1/2019 | Demiralp ............ A63B 24/0003 |
| 10,282,914 B1* | 5/2019 | Tran ..................... A61B 5/1036 |
| 10,293,565 B1* | 5/2019 | Tran ......................... A43D 1/02 |
| 10,299,722 B1* | 5/2019 | Tran ....................... B33Y 80/00 |
| 10,531,965 B2* | 1/2020 | Herr ..................... A61B 5/4851 |
| 10,863,928 B1 | 12/2020 | Mobbs et al. |
| 11,324,655 B2* | 5/2022 | De Rossi ................. A61F 2/72 |
| 11,957,457 B2* | 4/2024 | Sonntag ................. A61B 5/112 |
| 2003/0069714 A1 | 4/2003 | Wigley et al. |
| 2003/0163287 A1 | 8/2003 | Vock et al. |
| 2004/0039254 A1 | 2/2004 | Stivoric et al. |
| 2004/0122334 A1 | 6/2004 | Yamashiro |
| 2004/0167390 A1 | 8/2004 | Alexander et al. |
| 2005/0010139 A1* | 1/2005 | Aminian .............. A61B 5/1038 600/595 |
| 2005/0010299 A1 | 1/2005 | Disilvestro |
| 2005/0010301 A1 | 1/2005 | Disilvestro et al. |
| 2005/0197540 A1 | 9/2005 | Liedtke |
| 2007/0143068 A1* | 6/2007 | Pasolini ............... G01C 22/006 702/160 |
| 2007/0167688 A1 | 7/2007 | Ross et al. |
| 2007/0250286 A1 | 10/2007 | Duncan et al. |
| 2008/0027296 A1 | 1/2008 | Hadvary et al. |
| 2008/0299960 A1 | 12/2008 | Lockhart et al. |
| 2008/0311765 A1 | 12/2008 | Chatterjee et al. |
| 2009/0309683 A1 | 12/2009 | Cochran |
| 2010/0114596 A1 | 5/2010 | Williams et al. |
| 2010/0174189 A1 | 7/2010 | Abraham |
| 2010/0228089 A1 | 9/2010 | Hoffman et al. |
| 2010/0262047 A1 | 10/2010 | Genis |
| 2010/0324403 A1 | 12/2010 | Brister et al. |
| 2011/0046558 A1 | 2/2011 | Gravesen et al. |
| 2011/0208444 A1 | 8/2011 | Solinsky |
| 2011/0213275 A1 | 9/2011 | Boos et al. |
| 2011/0231208 A1 | 9/2011 | Kaplin |
| 2011/0245711 A1 | 10/2011 | Katra et al. |
| 2011/0288379 A1 | 11/2011 | Wu |
| 2012/0143135 A1 | 6/2012 | Cole et al. |
| 2012/0253234 A1* | 10/2012 | Yang .................... A61B 5/1038 600/595 |
| 2013/0211259 A1 | 8/2013 | Komistek et al. |
| 2013/0217998 A1 | 8/2013 | Mahfouz et al. |
| 2014/0015687 A1 | 1/2014 | Narasimhan et al. |
| 2014/0049911 A1 | 2/2014 | Corbin et al. |
| 2014/0100464 A1 | 4/2014 | Kaleal et al. |
| 2014/0114453 A1 | 4/2014 | Bentley |
| 2014/0128778 A1 | 5/2014 | Chan et al. |
| 2014/0142864 A1 | 5/2014 | Spears et al. |
| 2014/0157911 A1 | 6/2014 | Sarrafzadeh et al. |
| 2014/0274413 A1 | 9/2014 | Chelst |
| 2014/0275815 A1 | 9/2014 | Stein et al. |
| 2014/0316526 A1 | 10/2014 | Grotz |
| 2014/0358193 A1 | 12/2014 | Lyons et al. |
| 2015/0003699 A1 | 1/2015 | Davis et al. |
| 2015/0019135 A1 | 1/2015 | Kacyvenski et al. |
| 2015/0045700 A1 | 2/2015 | Cavanagh et al. |
| 2015/0230183 A1 | 8/2015 | Stogaitis et al. |
| 2015/0238094 A1 | 8/2015 | Lai et al. |
| 2015/0282796 A1 | 10/2015 | Nawana et al. |
| 2015/0302162 A1 | 10/2015 | Hughes et al. |
| 2016/0007861 A1 | 1/2016 | Tseng et al. |
| 2016/0066843 A1 | 3/2016 | Mensinger et al. |
| 2016/0077596 A1 | 3/2016 | Pantelopoulos et al. |
| 2016/0220176 A1 | 8/2016 | Desnerck et al. |
| 2016/0302674 A1 | 10/2016 | Moyer et al. |
| 2016/0302721 A1 | 10/2016 | Wiedenhoefer et al. |
| 2016/0310066 A1 | 10/2016 | Wiedenhoefer et al. |
| 2017/0143261 A1 | 5/2017 | Wiedenhoefer et al. |
| 2017/0147789 A1 | 5/2017 | Wiedenhoefer et al. |
| 2017/0181698 A1 | 6/2017 | Wiedenhoefer et al. |
| 2017/0241797 A1 | 8/2017 | Kong et al. |
| 2017/0244827 A1 | 8/2017 | Kang et al. |
| 2017/0273601 A1 | 9/2017 | Wang et al. |
| 2018/0116572 A1 | 5/2018 | Simpson et al. |
| 2018/0177436 A1 | 6/2018 | Chang et al. |
| 2018/0199674 A1 | 7/2018 | Walker et al. |
| 2018/0220935 A1* | 8/2018 | Tadano ..................... A61B 5/11 |
| 2019/0046078 A1* | 2/2019 | Lim ....................... B25J 9/0006 |
| 2019/0259475 A1* | 8/2019 | Dohrmann ................ G06T 7/70 |
| 2019/0336825 A1 | 11/2019 | Douglas et al. |
| 2020/0008712 A1* | 1/2020 | Takenaka ................. A61H 3/00 |
| 2020/0015712 A1* | 1/2020 | Hayashida ......... G08B 21/0446 |
| 2020/0163621 A1* | 5/2020 | Connor .................. A61B 5/389 |
| 2020/0367823 A1* | 11/2020 | Chahine ................. A41B 11/00 |
| 2021/0244318 A1* | 8/2021 | Sashen ................. A61B 5/1123 |
| 2021/0401325 A1* | 12/2021 | Fukushi ................. A61B 5/112 |
| 2022/0183588 A1* | 6/2022 | Fukushi ............... A61B 5/6807 |
| 2023/0009480 A1* | 1/2023 | Huang ................... G06Q 50/10 |
| 2023/0040492 A1* | 2/2023 | Huang ................. A61B 5/6807 |

FOREIGN PATENT DOCUMENTS

| | | |
|---|---|---|
| CN | 104068831 | 10/2014 |
| EP | 1938749 | 7/2008 |
| JP | 2012090946 | 5/2012 |
| JP | 2012110573 | 6/2012 |
| JP | 2012-223452 | 11/2012 |
| JP | 2013013579 | 1/2013 |
| JP | 2014138661 | 7/2014 |
| JP | 2015062654 | 4/2015 |
| KR | 20160033828 | 3/2016 |
| WO | 94/26359 | 11/1994 |
| WO | 2008/120215 | 10/2008 |
| WO | 2010/088696 | 8/2010 |
| WO | 2013/072234 | 5/2013 |
| WO | 2015/127218 | 8/2015 |
| WO | 2016/191753 | 8/2015 |
| WO | 2016/029138 | 2/2016 |

OTHER PUBLICATIONS

Official Communication for U.S. Appl. No. 16/927,561 mailed Aug. 18, 2022.

Official Communication for U.S. Appl. No. 15/422,320 mailed Jun. 16, 2022.

Official Communication for U.S. Appl. No. 16/813,548 mailed Mar. 30, 2022.

Jorleeds Medical: "Orthophysical App—Gyroscope Test", Nov. 29, 2016 (Nov. 29, 2016), pp. 1-3, XP054980919, Retrieved from the Internet: URL:https://www.youtube.com/watch?v=buUqo9E35Mk [retrieved on Sep. 9, 2020].

Nejati Hossein et al: "Smartphone and Mobile Image Processing for Assisted Living: Health-monitoring apps powered by advanced mobile imaging algorithms". IEEE Signal Processing Magazine. IEEE Service Center. Piscataway. NJ. US. vol. 33. No. 4. Jul. 1, 2016 (Jul. 1, 2016). pp. 30-48.

Rehamm Abo Elrahim et al: II Inter-rater and intra-rater reliability of Kinovea software for measurement of shoulder range of motion. Bulletin of Faculty of Physical Therapy. vol. 21. No. 2. Jan. 1, 2016 (Jan. 1, 2016). p. 80.

(56) References Cited

OTHER PUBLICATIONS

Giorgio Ferriero et al: "Reliability of a smartphone-based goniometer for knee joint goniometry :", International Journal of Rehabilitation Research, vol. 36, No. 2, Jun. 1, 2013 (Jun. 1, 2013), pp. 146-151.
"Emerging technologies—an imaging pill for gastrointestinal endoscopy", IEEE Engineering in Medicine and Biology Magazine, IEEE Service Center, Pisacataway, NJ, US, vol. 24, No. 4, Jul. 1, 2005 (Jul. 1, 2005), pp. 12-14.
Lenaerts B et al: "An Omnidirectional Transcutaneous Power Link for Capsule Endoscopy", Wearable and Implantable Body Sensor Networks, 2006. BSN 2006. International Workshop On Cambridge, MA, USA Apr. 3-5, 2006, Piscataway, NJ, USA, IEEE, Apr. 3, 2006 (Apr. 3, 2006), pp. 46-49.
Martinson et al., "Implementation of motion capture support in smartphones," Department of Computer Science and Engineering, Chalmers University of Technology, Jan. 1, 2010, Retrieved from the Internet at http://studentarbeten.chalmers.se/publication/129442-implementation-of-motion-capture-support-in-smartphones.
Official Communication for U.S. Appl. No. 16/775,026 mailed Mar. 6, 2020.
International Search Report and Written Opinion for PCT Application No. PCT/US2021/015520 mailed Mar. 26, 2021.
Official Communication for U.S. Appl. No. 15/077,793 mailed Nov. 29, 2021.
Official Communication for U.S. Appl. No. 15/422,320 mailed Nov. 26, 2021.

\* cited by examiner

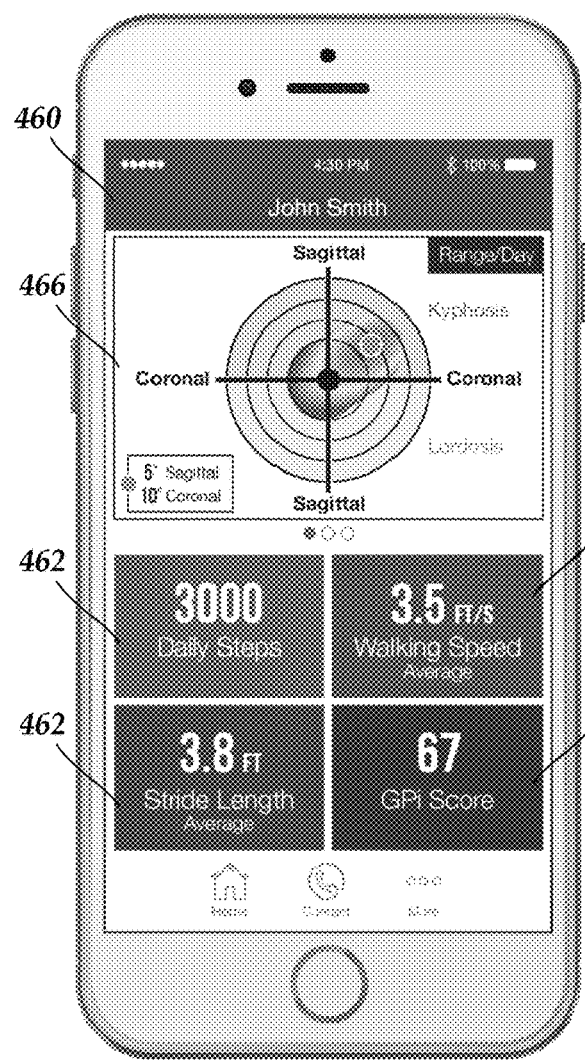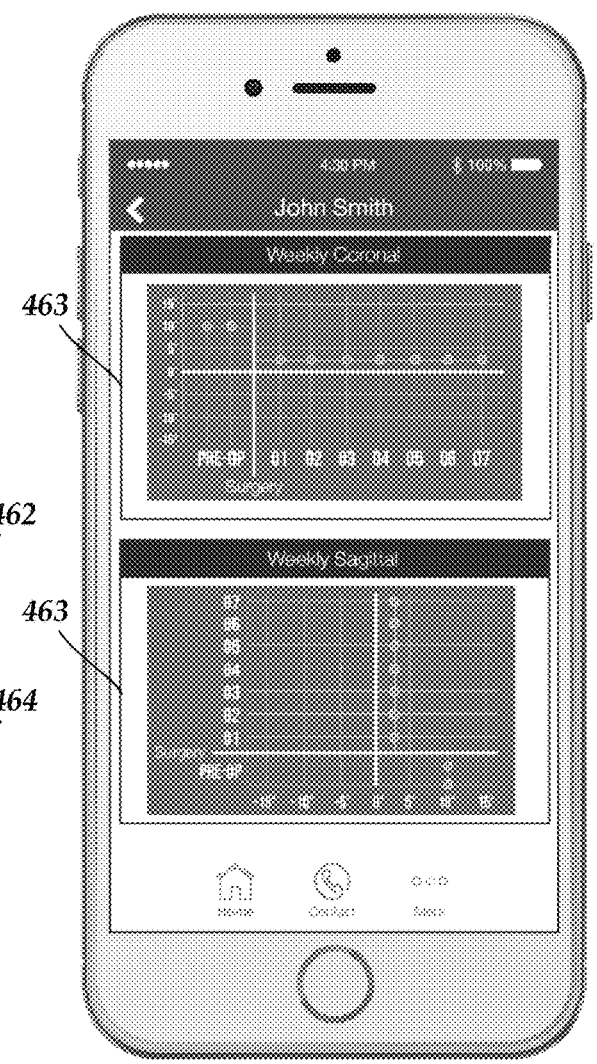
Fig. 4                    Fig. 5

SYSTEM AND METHODS FOR MONITORING THE SPINE, BALANCE, GAIT, OR POSTURE OF A PATIENT

CROSS-REFERENCE TO RELATED APPLICATION(S)

This application is a continuation of U.S. patent application Ser. No. 16/775,026, filed Jan. 28, 2020, which issued as U.S. Pat. No. 10,863,928, which is incorporated herein by reference in its entirety.

FIELD

The present invention is directed to the area of patient monitoring, physical therapy, and rehabilitation. The present invention is also directed to systems and methods for monitoring the spine, balance, gait, or posture of a patient.

BACKGROUND

The diagnosis, treatment, and management of musculoskeletal patients in the contemporary health care environment is challenging. The lack of an objective scoring system based on key metrics and meaningful real time data streams contribute to the challenges. The current classification system relies on subjective data which has influences based on the health care provider's and patient's own opinion rather than objective evidence.

Monitoring outcomes of spinal treatment or surgery is important and guides further treatment. The postoperative assessment of patient outcome, the individual performance of the patient, and the confirming of the validity of the interventions performed are facilitated by observations and measurement. However, the majority of published data has been based on subjective outcome tools such as the Oswestry Disability Index (ODI)/Neck Disability Index (NDI), Japanese Orthopaedic Association (JOA) score or the visual analogue scale (VAS). Unfortunately, subjective tools that capture this information are fraught with bias, timing issues, daily variance, and compliance, and are limited by their subjective nature.

BRIEF SUMMARY

One embodiment is a system for monitoring a user that includes a sensor unit configured and arranged to be disposed on the user, the sensor unit including an accelerometer and a communication arrangement; and at least one processor configured and arranged for performing actions including: receiving signals from the accelerometer of the sensor unit; determining a step count from the signals; determining a gait velocity from the signals; determining a step distance from the signals; determining a posture of the user from the signals; and determining a gait posture index as a function of the step count, gait velocity, step distance, and posture.

In at least some embodiments, the at least one processor includes a sensor processor disposed in the sensor unit. In at least some embodiments, the system further includes a patient device including a display and a communication arrangement configured for communication with the sensor unit. In at least some embodiments, the at least one processor includes a sensor processor disposed in the sensor unit and a patient device processor disposed in the patient device, wherein the actions further include displaying the gait posture index on the display of the patient device.

In at least some embodiments, the system further includes a clinician device including a display and a communication arrangement configured for communication with the sensor unit. In at least some embodiments, the at least one processor includes a sensor processor disposed in the sensor unit and a clinician device processor disposed in the clinician device, wherein the actions further include displaying the gait posture index on the display of the clinician device.

In at least some embodiments, determining the gait posture index includes determining a score for each of the step count, gait velocity, step distance, and posture using the measurements and combining the scores to obtain the gait posture index. In at least some embodiments, combining the scores includes weighting the scores and adding the weighted scores together to determine the gait posture index. In at least some embodiments, determining the score includes determining the score for a one of the measurements by determining a position of the measurement between a minimum value and a maximum value for the measurement. In at least some embodiments, the actions further include performing an action selected from providing a warning to the user or a clinician if the gate posture index meets a threshold criterion; altering a treatment, a physical therapy regimen, or an exercise regimen based on the gait posture index; recommending an alteration of a treatment, a physical therapy regimen, or an exercise regimen based on the gait posture index; or providing a preliminary or final diagnosis based on the gait posture index.

Another embodiments is a system for monitoring a user that includes a sensor unit configured and arranged to be disposed on the user, the sensor unit including an accelerometer and a communication arrangement; and at least one processor configured and arranged for performing actions including: receiving signals from the accelerometer of the sensor unit; determining a gait velocity from the signals; determining a posture deviation from the signals; and determining a fall prediction score as a function of the step count and gait velocity.

In at least some embodiments, the at least one processor includes a sensor processor disposed in the sensor unit. In at least some embodiments, the system further includes a patient device including a display and a communication arrangement configured for communication with the sensor unit. In at least some embodiments, the at least one processor includes a sensor processor disposed in the sensor unit and a patient device processor disposed in the patient device, wherein the actions further include displaying the fall prediction score on the display of the patient device.

In at least some embodiments, the system further includes a clinician device including a display and a communication arrangement configured for communication with the sensor unit. In at least some embodiments, the at least one processor includes a sensor processor disposed in the sensor unit and a clinician device processor disposed in the clinician device, wherein the actions further include displaying the fall prediction score on the display of the clinician device.

In at least some embodiments, determining the fall prediction score includes determining a score for each of the step count and posture deviation using the measurements and combining the scores to obtain the fall prediction score. In at least some embodiments, combining the scores includes weighting the scores and adding the weighted scores together to determine the fall prediction score. In at least some embodiments, determining the score includes determining the score for a one of the measurements by determining a position of the measurement between a minimum value and a maximum value for the measurement. In at least some embodiments, the actions further include performing an action selected from provide a warning to the user or a clinician if the gate posture index meets a threshold criterion; altering a treatment, a physical therapy regimen, or an exercise regimen based on the fall prediction score; recommending an alteration of a treatment, a physical therapy regimen, or an exercise regimen based on the fall prediction score; or providing a preliminary or final diagnosis based on the fall prediction score.

In other embodiments, the system can be used to determine metrics, described in detail below, other than the gait posture index or the fall prediction score.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 4 is a diagram of one embodiment of a user interface for a mobile device to display information obtained from a sensor unit, according to the invention;

FIG. 5 is a diagram of one embodiment of a user interface for a mobile device to display a range of motion measurement, according to the invention;

DETAILED DESCRIPTION

The present invention is directed to the area of patient monitoring, physical therapy, and rehabilitation. The present invention is also directed to systems and methods for monitoring the spine, balance, gait, or posture of a patient.

A system, as described herein, can be used to monitor the patient's physical activity or health, to monitor recovery from surgery or other treatment, to monitor the healing process, to monitor physical therapy or rehabilitation of the patient after treatment, or to monitor or verify the extent of the patient's activity, or any combination of these purposes. Systems for the monitoring of joint rehabilitation and physical therapy have been described in U.S. Patent Applications Publication Nos. 2016/0302721; 2016/0310066; 2017/0143261; 2017/0147789; and 2017/0181698, all of which are incorporated herein by reference. A similar system can be used to monitor a patient's spine, balance, gait, posture or the like. Instead of placing a sensor device of the system near a joint, such as the knee, the sensor device can be placed on the chest or back or the like.

The system includes one or more sensors that can communicate with a processor that can produce information, based on the sensor readings and data, to facilitate the patient or another user, such as a clinician, doctor, physical therapist, nurse, care coordinator, or other appropriate person, monitoring, for example, the patient's activity, spine, balance, gait, posture or the like. It will be understood, however, that the systems, devices, and methods described herein can be used for monitoring other conditions or making other measurements.

The system includes a wearable sensor unit with one or more sensors. For example, one or more sensors may be provided on a wearable sensor unit that is applied to the skin of the patient. In at least some embodiments, the one or more sensors communicate with a sensor processor in the sensor unit. In at least some embodiments, the sensor processor, or, alternatively or additionally, the sensors, communicate with a processor of a patient device, such as a mobile phone, tablet, computer, or the like, or with a processor of a clinician device, such as a mobile phone, tablet, computer, or the like.

Figure 1:
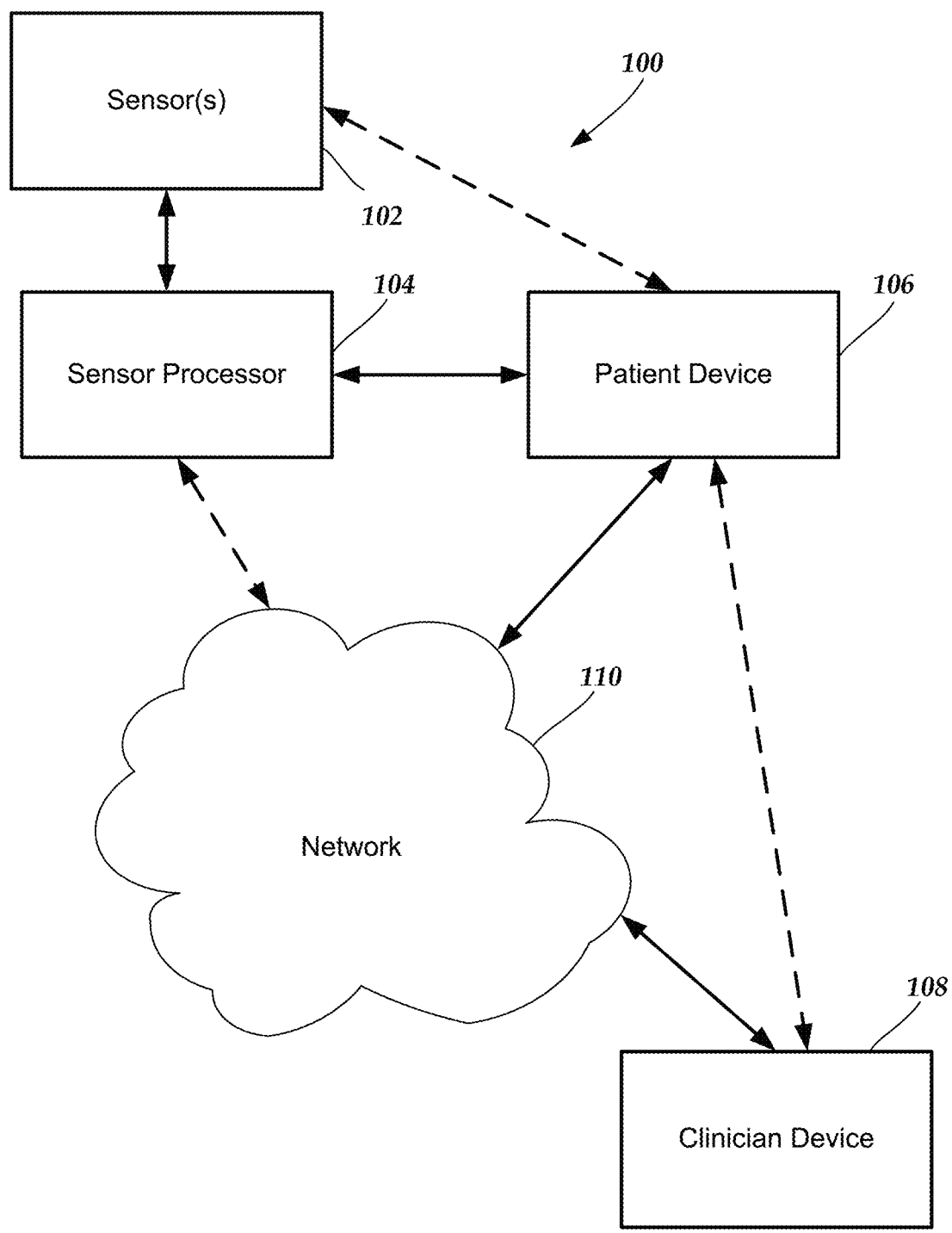
FIG. 1 is a schematic diagram of one embodiment of a system for monitoring rehabilitation of a patient after implant surgery, according to the invention.

FIG. 1 illustrates one embodiment of a system 100 for monitoring, for example, a patient's spine, balance, gait, posture, or the like. The system 100 includes one or more sensors 102, an optional sensor processor 104, a patient device 106 (such as a mobile phone, tablet, computer or the like), a clinician device 108, and a network 60. In at least some embodiments, the one or more sensors 102 and, preferably, the sensor processor 104 (or one or more of multiple sensor processors) are provided in a sensor unit that is external to the patient such as, for example, a device that is applied to the skin of the patient or is carried in an article or textile that is worn by the patient.

Other embodiments of the system may include fewer or more components than those illustrated in FIG. 1, but the system typically includes the sensor(s) 102 and a processor (such as one or more of the sensor processor 104, patient device 106, or clinician device 108) to communicate with the sensor(s) and provide information based on the sensor data. A sensor unit can include the sensors 102 and sensor processor 104, but it will be understood that other sensors may be included that are not part of the sensor unit. For example, one or more additional sensors may be combined into another wearable device that may or may not include a sensor processor. It will also be understood that, in some embodiments, the sensor unit may not include a sensor processor 104 or the sensor processor 104 may have limited capabilities (such as, for example, obtaining and transmitting sensor readings without (or with limited) analysis of the sensor readings)

In FIG. 1, the solid lines indicate communication between components in at least some embodiments of the system. Dotted lines indicate alternative or additional modes of communication between components. In addition to the communication illustrated in FIG. 1, in at least some embodiments, the sensor processor 104 or sensors 102 may also communicate directly with the clinician device. Communications can include, but is not limited to, wireless communication, wired communication, optical communication, ultrasonic communication, or the combination thereof. Satellite communication, cellular communication, Bluetooth™, near field communications (NFC), Infrared Data Association standard (IrDA), wireless fidelity (WiFi), and worldwide interoperability for microwave access (WiMAX) are non-limiting examples of wireless communication that can be used for communications. Ethernet, digital subscriber line (DSL), fiber to the home (FTTH), and plain old telephone service (POTS) are non-limiting examples of wired communication that can be used for communications.

The network 60 can be any suitable type of network including, but not limited to, a personal area network (PAN), local area network (LAN), metropolitan area network (MAN), wide area network (WAN), the Internet, or any combination thereof. In at least some embodiments, the network 60 can be bypassed to provide direct connection between components. It will be understood that other devices, such as a server or server farm, memory storage device, or the like can be connected to the patient device 106 or clinician device 108 through the network 60 or directly. For example, a server may be coupled to the patient device 106 or clinician device 108 that stores patient or other medical information, applications, user interfaces, a web interface, or the like for access by the patient device 106 or clinician device 108.

The patient device 106 and the clinician device 108 can be any suitable device such as, for example, computers (for example, a notebook computer, a mobile medical station or computer, a server, a mainframe computer, or a desktop computer), mobile devices (for example, a cellular phone or smartphone, personal digital assistant, or a tablet), or any other suitable device. In at least some embodiments, the clinician device 108 can be incorporated into a medical station or system.

Figure 2:
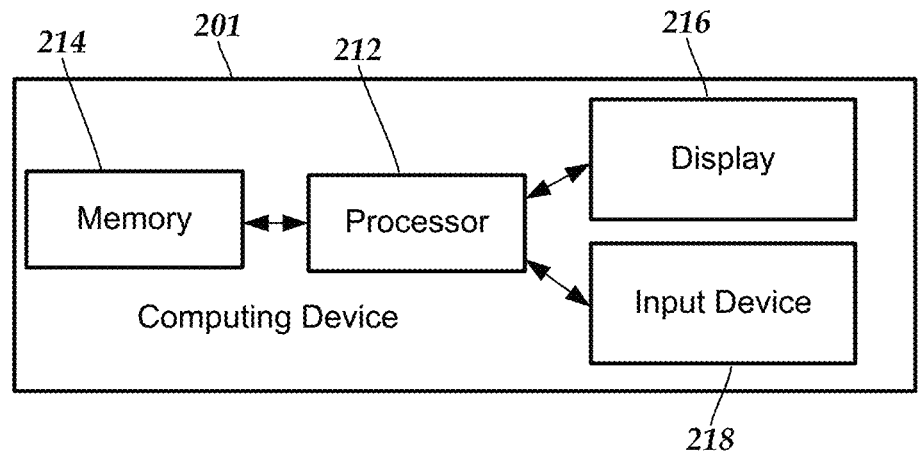
FIG. 2 is a schematic diagram of one embodiment of a computing device for use in the system of FIG. 1, according to the invention.

FIG. 2 illustrates one embodiment of a computing device 201 for use as the patient device 106 or clinician device 108. The computing device 201 includes a processor 214 and a memory 216, a display 218, and an input device 220. The computing device 201 can be local to the user or can include components that are non-local to the computer including one or both of the processor 214 or memory 216 (or portions thereof). For example, in some embodiments, the user may operate a terminal that is connected to a non-local processor or memory.

The computing device 201 can utilize any suitable processor 214 including one or more hardware processors that may be local to the user or non-local to the user or other components of the computing device. The processor 214 is configured to execute instructions provided to the processor. Such instructions can include any of the steps of methods or processes described herein.

Any suitable memory 216 can be used for the computing device 214. The memory 216 illustrates a type of computer-readable media, namely computer-readable storage media. Computer-readable storage media may include, but is not limited to, nonvolatile, non-transitory, removable, and non-removable computer-readable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, Bluetooth™, near field communication, and other wireless media.

The display 218 can be any suitable display device, such as a monitor, screen, display, or the like, and can include a printer. The input device 220 can be, for example, a keyboard, mouse, touch screen, track ball, joystick, voice recognition system, camera, microphone, or any combination thereof, or the like.

Returning to FIG. 1, the sensor processor 104 can be any suitable processor including one or more hardware processors. The sensor processor 104 is configured to execute instructions provided to the processor. The sensor processor 104 is configured to receive sensor data from the sensor(s) and communicate with the patient device 106, network 60, clinician device 108, or any combination thereof. Optionally, the sensor processor 104 may also process or analyze the sensor data and may have instructions stored thereon to perform such processing or analysis including, for example, instructions to perform the steps of any of the processing or analysis described herein. In at least some embodiments, one or more of the sensor(s) 102 can each include a processor that perhaps some or all of the functions of the sensor processor 104.

Any suitable type of sensor 102 can be used including, but not limited to, accelerometers, magnetometers, gyroscopes, proximity sensors, infrared sensors, ultrasound sensors, thermistors or other temperature sensors, cameras, piezoelectric or other pressure sensors, sonar sensors, external fluid sensor, skin discoloration sensor, pH sensor, microphone, smoke or nicotine sensor, or the like or any combination thereof. In at least some embodiments, the system 100 includes at least one, two, three, four, five, six, or more different types of sensors 102. The system may include at least one, two, three, four, five, six, eight, ten, or more sensors 102. Further examples of suitable sensors and their arrangement and use can be found at U.S. Patent Applications Publication Nos. 2016/0302721; 2016/0310066; 2017/0143261; 2017/0147789; and 2017/0181698, all of which are incorporated herein by reference.

The one or more sensors 102 can be used to measure, monitor, or otherwise observe a patient's physical activity or health; recovery from surgery or other treatment; healing after injury, surgery, or treatment; physical therapy or rehabilitation of the patient after injury, surgery, or treatment; or patient activity, or any combination thereof. The following are examples of observations or measurements that can be made or interpreted using one or more of the sensors: number of steps, gait velocity (speed), gait distance, sagittal posture, coronal posture, exercise repetitions or regimens, rate of motion, temperature of skin, pulse or pulse profile or heart rate recovery time after activity, sleep profile or rest duration, gait analysis, body/limb/joint alignments, heart rate, oxygen level, or the like. A system 100 can observe or measure one or more of these items or any combination of the items.

Figure 3:
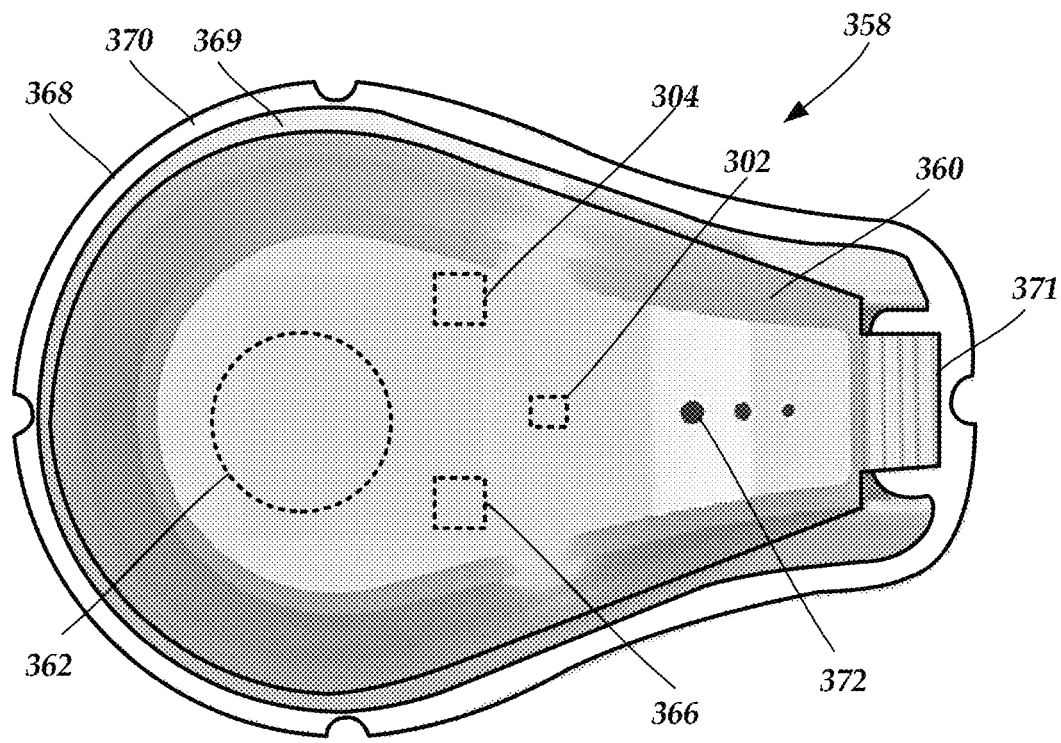
FIG. 3 is a top view of one embodiment of a sensor module that contains sensors for monitoring rehabilitation of a patient, according to the invention.

FIG. 3 illustrates one embodiment of a sensor unit 358 that can be adhered, or otherwise placed adjacent, to the skin of the patient. The sensor unit includes a housing 360 and a base 370 (or other skin-mounting arrangement) with a receiving shell 369 for attachment of the housing and an adhesive pad 368 to attach the base to the skin of the patient. Within the housing 360 the sensor unit 358 include one or more sensors 302, a power source 362, a communications unit 366, and sensor processor 304.

The housing 360 can be made of any suitable material, such as plastic materials (for example, silicone), and preferably has sufficient flexibility to fit comfortably on the patient's skin following the anatomical contours and to also flex as the patient moves. In at least some embodiments, the housing 360 is also water resistant to resist ingress of sweat, rain, and other fluids into the interior of the housing. In at least some embodiments, the housing 360 is sufficiently water resistant to allow the patient to shower with the sensor unit 358 remaining attached to the skin of the patient and without any covering over the sensor unit. In some embodiments, the housing 360 is sufficiently water resistant to allow the patient to bathe or swim without any covering over the sensor unit 358. In at least some embodiments, the housing 360 may include a tab 371 that can facilitate removal of the housing 360 from the base 370.

In at least some embodiments, the housing 360 has a shape or indicia on the housing that visually indicates or suggests the orientation of the device when the housing is attached to the patient. In the illustrated embodiment, one end of the device is narrower than the other end which indicates or suggests to the user that the narrow end is pointed downward, toward the legs.

The sensors 302, power source 362, communications unit 366, and sensor processor 304 can be disposed within the housing 360. In some embodiments, a portion of one or more of the sensors, such as a temperature, pulse, or pressure sensor; moisture sensor, strain gage, may extend through the housing to provide contact with the skin or access to the patient without an intervening portion of the housing 360 or other parts of the sensor unit 358. In some embodiments of the sensor unit 358, the sensors can include an accelerometer and a gyroscope. The accelerometer and gyroscope can be used to measure number of steps, gait velocity (speed), gait distance, sagittal posture, coronal posture, and the like. Other suitable sensors include, but are not limited to, a microphone, pulse oximetry sensor, a heart rate monitor, or the like, or any combination thereof. As will be understood, any suitable sensor described above can be included in the sensor unit and any combination of those sensors can be used in the sensor unit.

Power can be provided to the sensors 302 and sensor processor 304 using any suitable power source 362 including, but not limited to, primary cells, coin cell batteries, rechargeable batteries, storage capacitors, other power storage devices, or the like or any combination thereof. In some embodiments, the power can be provided by a kinetic energy power source that utilizes the movements of the patient's body to generate power for the components or to or to charge a battery or storage capacitor or other power storage device coupled to the components. In some embodiments, wireless power sources can be used in place of (or in addition to) the battery, storage capacitor, or other power storage device.

In addition, a charging port can be provided for charging the battery or storage capacitor or other power storage device from a source such as a wall socket. Alternatively or additionally, wireless charging systems and methods can also be used. It will be understood that in some embodiments there may be multiple methods for providing power to the component or to a power storage device associated with the component. All of the sensors and the sensor processor may be coupled to the same power source or some of the sensors (or even all of the sensors) and sensor processor may have individual power sources.

In at least some embodiments, the power source 362 can be a primary cell and may have an expected lifetime under normal usage of at least 1, 2, or 4 weeks or at least 1, 2, 3, 4, 6, 8, 10, 12, 15, 18, 24, months or more. In at least some embodiments, the power source 362 is rechargeable using, for example, a recharge port in the sensor unit 358 or is capable of being wirelessly charged such as with an inductive recharge device (such as an inductive mat or sleeve), or using WiFi or ultrasonic charging as described above. (In some embodiments, the recharge device may be connected to a network to retrieve data or measurements or signals from the sensor unit and transmit them to a patient device, clinician device, or other device for use or storage or the like.) The power could be provided to the device by energy harvesting means, such as with cantilevered piezo reeds, a generator and pendulum setup, passive magnets rolling/sliding/bouncing through or by coils, or the like to convert some amount of kinetic energy into electrical energy to be used by the device. The power source 362 provides power to the sensors 302, communications unit 366, sensor processor 304, and any other components in the sensor unit.

In at least some embodiments, the sensors 302 and sensor processor 304 can be active at all times to measure, monitor, or otherwise observe. In other embodiments, one or more of the sensors 302 and sensor processor 304 can be active periodically (with a period of, for example, 15 or 30 seconds or 1, 5, 10, 15, or 30 minutes or 1, 2, 3, 4, 6, 7, or 24 hours) or randomly to measure, monitor, or otherwise observe. Optionally, the period may be programmable. In addition, the period may be optionally altered based on data from one or more of the sensors. In yet other embodiments, one or more of the sensors 302 and sensor processor 304 may be activated manually or automatically by the sensor module, patient device, clinician device, or other device. In at least some embodiments, the sensors and optional sensor processor may have different activation schedules (continuous, periodic, random, or manual). For example, a sensor to measure temperature may do so periodically, a sensor to measure number of steps or movement may be continuous, and a sensor to measure posture may be activated manually by the wearable device, patient device, or clinician device.

The illustrated embodiment also features a power light 372 that is lit when the sensor unit 358 is functioning to assure the patient that the device is operating. In some embodiments, the power light 372 may also flash or change color to indicate device functions such as, for example, a low battery, pairing with another device (for example, the patient device 106, clinician device 108, or network 110 of FIG. 1), actively taking readings using one or more of the sensors (particularly for sensors that are manually or periodically activated), alert the patient that it is time to perform exercises, change adhesives or the like.

In at least some embodiments, the housing 360 can include a power button (not shown) that can be activated to turn the device on and, optionally, to turn the device off. In at least some embodiments, the power button may also be activated to manually direct one or more of the sensors to take readings. In at least some embodiments, the sensor unit 358 can be turned on or off using the patient device or clinician device.

In other embodiments, the housing 360 may include a sensor, such as a color sensor or proximity sensor, that can detect when the housing 360 is attached to the base 370 to turn the sensor unit 358 on, when attached, or off, when not attached. For example, the sensor may detect a color of the base or may detect the proximity of the base to turn on the sensor unit 358. Alternatively, when the housing 360 is attached to the base 370, the sensor unit 358 may enter an activatable status so that the sensor unit 358 can be turned on manually or using a device such as the patient device or clinician device.

The base 370 is designed to hold the sensor unit 358 on the patient's skin. The adhesive pad 368 of the base 370 can have, for example, a substrate with adhesive on both sides of the substrate so that one side can be adhered to the patient's skin and the other side adhered to the housing 360. In at least some embodiments, the base 370 can be periodically replaced (for example, every 1, 2, 5, or 3 days or every 2, 3, 4, or more weeks) as the adhesive next to the patient's skin or the housing 360 may degrade or otherwise lose some or all of its adhesiveness. Preferably, at least the adhesive to be adhered to the patient's skin is selected to prevent or resist causing skin irritation. Preferably, the adhesive on both sides of the substrate is selected to be water resistant and resist losing adherence due to contact with sweat. In at least some embodiments, the base 370 extends around the circumference of the sensor unit 358 and optionally includes one or more openings so allow the housing 360 to make contact with the skin of the patient or access to the patient without an intervening portion of the base 370.

In other embodiments, instead of the base 370, adhesive may be applied directly to the housing for adhering the housing with the directly to the skin. In yet other embodiments, instead of adhering the sensor unit to the skin, the sensor unit can be inserted into an article to be worn by the patient and hold the sensor unit in place at the desired position on the body.

The sensor processor 304 can be any suitable processor and may include, or be coupled to, a memory unit for storing sensor data. The sensor processor 304 can be wired or wirelessly coupled to the sensor 302 for receiving data from the sensors. In some embodiments, the sensor processor 304 may include analysis algorithms for analyzing or partially analyzing the sensor data. In other embodiments, the sensor processor 304 may be primarily designed to receive, store, and transmit sensor data.

The communications unit 366 can be any suitable communications arrangement that can transmit information from the sensor processor 304 or sensors 302 to another device (such as the patient device 106, clinician device 108, or network 110 of FIG. 1.) The communications unit 366 can transmit this information by any suitable wired or wireless technique including, but not limited to, Bluetooth™, near field communications, WiFi, infrared, radio frequency, acoustic, optical, or using a wired connection through a data port in the sensor unit or any other communications technique presented herein or the like.

In at least some embodiments, the base 370 is sufficiently flexible for adhesion to the skin of a patient as the patient moves during normal activity or physical therapy exercises. The receiving shell 369 may be made of any suitable material including, but not limited to, flexible plastics such as silicone or polyurethane. In at least some embodiments, the receiving shell 369 removably grips the housing 360 to provide further maintenance of the attachment of the housing to the base 370. In at least some embodiments, the receiving shell 369 is resiliently flexible to expand when the portion of the housing 360 is received in the receiving shell and then to compress against a perimeter of the received portion of the housing.

The adhesive pad 368 can be adhesive applied to the receiving shell 369 or can be an adhesive disposed on two sides of a substrate with one side of the substrate adhered to the receiving shell 369. Preferably, the adhesive is selected to be water resistant and resist losing adherence due to contact with sweat. In at least some embodiments, the base 370 or the adhesive on the base is intended for use for at least one, two, three, five, seven, or ten days or two, three, or four weeks or more under normal usage conditions before replacement or reapplication of adhesive. In at least some embodiments, the adhesive is selected to maintain adhesion to the skin when the user takes a shower. In at least some embodiments, the adhesive is selected to maintain adhesion to the skin when the user takes a bath, swims in a pool, or sits in jacuzzi, hot tub, or rehabilitation pool.

Diagnosis, treatment and management of musculoskeletal patients can be challenging due, at least in part, to a lack of an objective scoring system based on key metrics and the lack of access to meaningful real time data streams. Conventional classification systems and arrangements often rely on subjective data which has influences based on the opinion of a health care provider or the patient or any combination of individuals.

In at least some embodiments, the systems and methods can track, quantify, and qualify musculoskeletal movement in real time. In at least some embodiments, the systems and methods can facilitate gauging a user's health prior to a surgical procedure and during the rehabilitation period following the procedure, as well as general monitoring after the rehabilitation period. In at least some embodiments, the system and methods can permit a physician, clinician, user, or other individual to observe and study a real time patient (or user) data stream and provide objective data on patients or users that are being diagnosed, evaluated for a treatment, evaluated after a treatment, or otherwise observed.

The systems and methods include obtaining or determining measurements of one or more user characteristics or activities. Examples include, but are not limited to number of steps, gait velocity (speed), gait distance, sagittal posture, coronal posture, exercise repetitions or regimens, or the like or any combination thereof. In at least some embodiments, one or more of these measurements can be performed continuously or over an extended length of time such as, for example, measuring the number of steps over a period of 1, 2, 4, 6, 8, 12, or 24 hours (or any shorter or longer length of time.) In at least some embodiments, one or more of the measurements may be performed when requested by the user, a clinician or other individual such as, for example, gait velocity (speed), gait distance, sagittal posture, coronal posture, exercise repetitions or regimens (that could include, for example, aquatic activity, stair exercise regiment, treadmill activity, or bicycle activity), or the like, or any combination thereof. In at least some embodiments, one or more the measurements may be made periodically or randomly, such as, for example, gait velocity (speed), gait distance, sagittal posture, coronal posture, fall prediction, pain score, wound photo, or the like or any combination thereof. In some of these instances, the measurement may only be performed when the user is engaged in an activity such as standing or walking. The system or method may include a determination that the user is engaged in the activity prior to making the measurement.

The systems and methods described herein utilize models to characterize user health, treatment, rehabilitation, or the like and includes the determination of one or more model-based metrics from the measurements. The systems, methods, and models can be used to produce objective measures of, for example, musculoskeletal movement, potential disease or disorder states, treatment efficacy, rehabilitation progress, improvement, decline over time, or general (or musculoskeletal) health. The systems, methods, and models may be also used to, for example, monitor or classify musculoskeletal deficiency, including, for example, classifying the severity of pain, damage, degeneration, disorders, diseases, or other issues.

The systems and methods can include one or more models that utilize personal characteristics and one or more measurements to determine one or more model-based metrics. The personal characteristics can include one or more of the following: age, gender, height, weight, level of activity, level of mobility, body mass index (BMI), implant type, surgical procedure, instrumentation, or the like or any combination thereof. The model-based metric is determined using two or more of the measurements in a specified or predetermined combination. In at least some embodiments, the model-based metric includes a combination of multiple scores, where each score is based on one or more of the measurements and may include a determination of where the measurement(s) fall within a specified or predetermined range. In at least some embodiments, the specified or predetermined range for one or more of the scores (or the score itself) may depend on one or more of the personal characteristics. For example, a range for a measurement or a score may differ based on the gender, age, or height (or any other personal characteristic or combination of personal characteristics) of the user.

In at least some embodiments, the score is based on where the measurement falls within a predetermined range. As an example, the range can have a minimum value, $x_0$, (which may be 0) and a maximum value, $x_1$ and the maximum score can be represented as A. In some embodiments, the score, $S_m$, can be linear function so that, for a given measurement $x_m$ (which falls within the range), $S_m = A*(x_m - x_0)/(x_1 - x_0)$. In at least some embodiments, if $x_m > x_1$ then the score $S_m = A$ and if $x_m < x_0$ then the score $S_m = 0$. The score may also be a non-linear function (for example, an exponential, logarithmic, step, multi-step, triangular, or other function) of the measurement or can be composite function with multiple ranges, each range having a linear or non-linear relationship to the measurement.

A model-based metric can be determined from one or more (preferably, two or more) of the scores. In at least some embodiments, a metric, M, can be a weighted combination (with weights, $w_1, w_2, \ldots$) of scores, $S_1, S_2, \ldots$ so that $M = w_1*S_1 + w_2*S_2 + \ldots$. In some embodiments, the weights may all be equal to each other. In other embodiments, the weights can be different for two or more of the scores. In at least some embodiments, instead of (or in addition to) using weights, the maximum value for each of the scores can differ from one or more of the other scores. It will be understood that in all of the examples described herein variation in the maximum score can be used as an alternative to the use of weights for the different scores.

Each of the model-based metrics, or the model associated with the metric, can differ from other metrics, or model, by changing one or more of the selection of measurements, selection of ranges, form of the score equation (e.g., linear, non-linear, etc.), weights for the different scores, and the like. For example, one model or metric may be generated for a 60 to 70 year old man and a different model or metric generated for a middle-aged woman by changing one or more of the ranges for the measurements used to generate the scores. Thus, the systems and methods can utilize a number of different models or metrics that depend on personal characteristics. Additionally, other models or metrics may differ for reasons other than personal characteristics. For example, the score weights may differ between two or more models or metrics to place different emphasis on the individual measurements.

In at least some embodiments, a system may automatically choose one of the models or metrics based on input data (such as one or more of the characteristics). In at least some embodiments, a system may allow the user or a clinician to select a model or metric. In at least some embodiments, the system may select or use a default model or metric, but also allow the user or a clinician to select a different model or metric. In at least some embodiments, the system may select a model or metric or a family of models or metrics automatically (for example, selecting a model or metric or family of models or metrics based on the input of personal characteristics of the user) and then allow modification or selection within the family by the user or clinician (for example, selecting models or metrics have different weights for the scores.)

Figure 13:
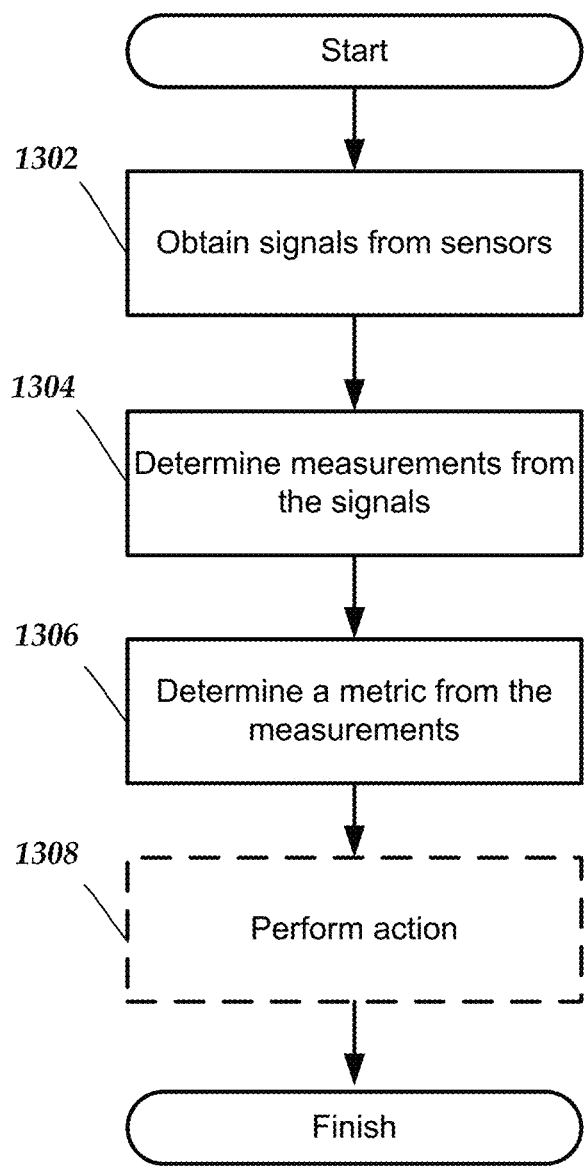
FIG. 13 is a flow chart of one embodiment of a method of monitoring a user, according to the invention.

FIG. 13 illustrates one embodiment of a method for monitoring a user. In step 1302, signals are obtained from one or more sensors. In some embodiments, the one or more sensors may all be on a sensor unit as described above. In other embodiments, one or more of the sensors are on the sensor unit and one or more of the sensors may be independent of the sensor unit.

In step 1304, measurements are determined from the signals. Examples of measurements include, but are not limited to, number of steps, gait velocity (speed), gait distance, sagittal posture, coronal posture, exercise repetitions or regimens (that could include, for example, aquatic activity, stair exercise regiment, treadmill activity, or bicycle activity), or the like or any combination thereof. In some embodiments, one or more of the measurements can be obtained directly from the signals. In some embodiments, one or more of the measurements may include analysis or processing of the signals to determine the measurement(s).

In step 1306, a metric is determined based on the measurements. Examples of metrics are provided below and include, but are not limited to, the gait posture index (GPi), fall prediction score (FPs), objective claudicant score (OCs), health gait index (HGi), or the like or any combination thereof.

In optional step 1308, a system or a user may perform an action in response to the determination of the metric. For example, the system or the user may provide a warning to the user or a clinician (for example, through the sensor unit, patient device, or clinician device) if the metric meets a threshold criterion; the system or the user may alter (or recommend alteration of) a treatment, a physical therapy regimen, or an exercise regimen based on the metric; the system or the user may provide a preliminary or final diagnosis based on the metric; or the like or any combination thereof.

As an example, in at least some embodiments, a system or method is used to determine a gait posture index (GPi). In at least some embodiments, the GPi is a metric that combines scores for the following measurements: step count, gait velocity, step distance, and posture into a composite metric that represents health and mobility. (It will be understood that this is merely an example and that a GPi can be generated using a different selection of measurements.) As one example, the GPi can have a rating from 0 to 100 with a maximum score of 25 assigned to each of the following four categories: step count, gait velocity, step distance, and posture. In this example, $GPi=25*(sc_m-sc_0)/(sc_1-sc_0)+25*(gv_m-gv_0)/(gv_1-gv_0)+25*(sd_m-sd_0)/(sd_1-sd_0)+25*(p_m-p_0)/(p_1-p_0)$ where the subscript m refers to a value of a measurement, the subscript 0 indicates that lower limit of the range for the measurement, the subscript 1 is the upper limit of the range for the measurement, and sc=step count, gv=gait velocity, sd=step distance, and p=posture.

As another example, the maximum score values may be asymmetrical with a maximum score of 20 points each for step count, gait velocity, and step distance and a maximum score of 40 points for posture. In this case, $GPi=20*(sc_m-sc_0)/(sc_1-sc_0)+20*(gv_m-gv_0)/(gv_1-gv_0)+20*(sd_m-sd_0)/(sd_1-sd_0)+40*(p_m-p_0)/(p_1-p_0)$ In at least some embodiments, the score for step count can be determined by measuring step count $sc_m$ over a period of time (such as daily or over 1, 2, 3, 4, 6, or 12 hours or 1, 5, 10, 15, 20, or minutes or any other suitable period of time). The range for the score can be, for example, $sc_0=0$ steps and $sc_1=10,0000$ steps (although any other suitable number of steps can be used and will depend on the length of time over which the steps are counted). As one example, the score is determined on the basis of a ratio of the daily step count over 10,000 steps. If the step count is equal to or greater the top of the range (e.g., 10,000 steps), then the full score is assigned.

In at least some embodiments, the score for gait velocity may be apportioned based on a comparison of one or more measurements by the system with a range of $gv_0=20$ cm/s to $gv_1=160$ cm/s (or any other suitable range). If the gait velocity is equal to or greater than $gv_1$ (e.g., 160 cm/s), then the full score is given. If the gait velocity is less than $gv_0$ (e.g., 20 cm/s), then a score of zero is given.

In at least some embodiments, the score for step distance (or stride length) may be apportioned based on a comparison of one or more measurements by the system with a range of $sd_0=0$ to $sd_1=80$ cm. If the step distance is equal to or greater than $sd_1$ (e.g., 80 cm), then the full score is given. In at least some embodiments, this range may be modified based on patient height or leg length.

In at least some embodiments, the score for posture may be apportioned based on a comparison of one or more measurements of the bend angle of the upper torso of the user by the system with a range of $p_0=30$ degrees to $p_1=0$ degrees. If the angle of the upper torso is equal to or greater than $sd_0$ (e.g., 30 degrees), then a score of zero points is given. In at least some embodiments, posture may include both sagittal (front-back) and coronal (left-right) measurements.

Walking is a fundamental part of living, and its importance is not limited by age, race, or medical status. The ability to walk and relative capability of walking can influence an individual's participation and interaction with society. Walking measurements can often be a relatively accurate assessment of health. A deterioration in walking measurements can be associated with a deterioration in health, and can correlate significantly with poor health outcomes. The GPi score described herein can be used for a variety of applications including, but not limited to, monitoring health status, assisting in diagnosis, monitoring recovery following surgical intervention or other treatment, guide rehabilitation, or the like or any combination thereof. In at least some embodiments, the GPi score is particularly useful for assessing or monitoring musculoskeletal and neurological problems as these tend to affect mobility as an initiating event.

In at least some embodiments, the ranges for the different measurements can be modified for age, gender, height, or other personal characteristics, or any combination thereof. The range of the final GPi metric in the example provided above is 0 to 100 where 0 indicates very poor health (possibly bed bound and non-ambulant) and 100 indicates good health. For instance, a healthy 85 year-old, who walks with an upright neutral posture, with good velocity and stride length, and remains active with high daily step count, would have a GPi in the range of 90-100 in this example. A sustained GPi score of zero may correlate with end stage health. A score of 100 correlates to a healthy individual, who walks a minimum of 10,000 s/day, a Gait Velocity (GV) within a normal range for their age, a Mean Stride Length (MSL) within a normal range for their height, and with an upright posture ("balance") with no lateral trunk deviation, or forward stoop/kyphosis. This scoring arrangement would not be suitable for paraplegic or quadriplegic individuals and may be modified for those who use walking aids. For example, patients with a single upper limb walking aid may subtract 5 from the metric or with two walking aids or a forearm support frame may subtract 10 from the metric.

Another metric is the cone of balance score (CBs). The CBs may combine measurements for ambulation, optionally in combination with measurements of coronal position and sagittal position. A high score indicates more time spent in a neutral position and a low score indicates more time spent with a gait deformity.

Figure 14:
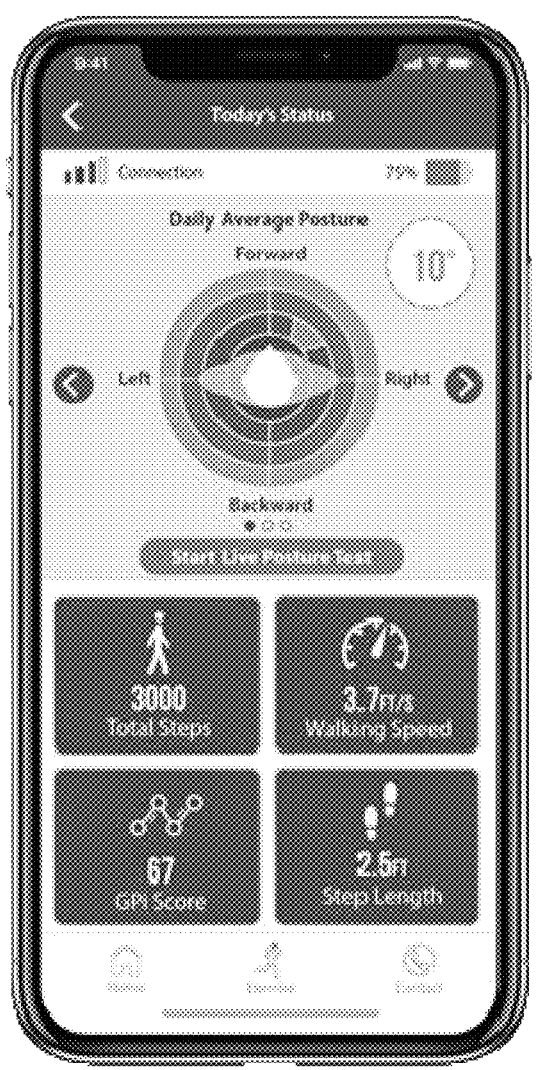
FIG. 14 is a diagram of a further embodiment of a user interface to display information obtained from a sensor unit, according to the invention.

In at least some embodiments, a score of zero (0) is perfect posture. Falling outside the cone of balance or a high score may place the patient at a high risk of a fall event. A low score indicates more time spent in a neutral position and a high score indicates more time spent with a gait deformity. As another example of scoring (which may be used to provide the posture component of the GPi metric), an average or measured posture angle from straight of 0 or 1 degrees provides a score of 25 out of 25. An average or measured posture angle of 2 to 5 degrees provides a score of 20. An average or measured posture angle of 6 to 10 degrees provides a score of 15. An average or measured posture angle of 11 to 15 degrees provides a score of 10. An average or measured posture angle of 16 degrees or greater provides a score of 5. FIG. 14 illustrates an interface (described in more detail below) where the daily posture score indicates 10 degrees stoop to the right and forward which would give a 15 out of 25 scoring for the posture score component of the overall GPi formula.

Another example of a metric is a Health Gait Index (HGi). In at least some embodiments, the HGi is a metric that combines scores for the following measurements: heart rate, gait velocity, sleep cycle, step count or activity, and posture (or cone of balance (CB)) into a composite metric that represents health and mobility. As one example, the HGi can have a rating from 0 to 100 with a maximum score of 20 assigned to each of the following five categories: heart rate, gait velocity, sleep cycle, step count or activity, and posture (or cone of balance (CB)). In this example, $HGi=20*(hr_m-hr_0)/(hr_1-hr_0)+20*(gv_m-gv_0)/(gv_1-gv_0)+20*(sc_m-sc_0)/(sc_1-sc_0)+20*(sl_m-sl_0)/(sl_1-sl_0)+20*(p_m-p_0)/(p_1-p_0)$ where the subscript m refers to a value of a measurement, the subscript 0 indicates that lower limit of the range for the measurement, the subscript 1 is the upper limit of the range for the measurement, and hr=heart rate, gv=gait velocity, sc=step count (or other activity measure), sl=sleep cycle, and p=posture.

Another example of a metric is an Objective Claudicant Score (OCs). In at least some embodiments, the OCs is a metric that combines scores for the following measurements: gait velocity, step count, sagittal balance, and time to walk. As one example, the OCs can have a rating from 0 to 100 with a maximum score of 25 assigned to each of the following four categories: gait velocity, step count, sagittal balance, and time to walk. In this example, $OCs=25*(gv_m-gv_0)/(gv_1-gv_0)+25*(sc_m-sc_0)/(sc_1-sc_0)+25*(sb_m-sb_0)/(sb_1-sb_0)+25*(tw_m-tw_0)/(tw_1-tw_0)$ where the subscript m refers to a value of a measurement, the subscript 0 indicates that lower limit of the range for the measurement, the subscript 1 is the upper limit of the range for the measurement, and gv=gait velocity, sc=step count, sb=sagittal balance, and tw=time to walk. In at least some embodiments, an OCs of 0 indicates no claudicant symptoms and an OCs of 100 indicates severe claudicant symptoms.

A further example of a metric is a fall prediction score (FPs). In at least some embodiments, the FPs is a metric that combines scores for the following measurements: gait velocity and posture deviation (from zero degrees relative to perfect posture) which may also be described as sway or wobble. As one example, the FPs can have a rating from 0 to 100 with a maximum score of 50 assigned to each of the following two categories: gait velocity and posture deviation (e.g., sway/wobble). In this example, instead of using a formula, scores are assigned to different ranges for each category. For example, in at least some embodiments, for gait velocity, a score of 15 is assigned for a gait velocity of 0 to 0.6 m/s; a score of 30 is assigned for a gait velocity of 0.6 to 0.90 m/s; a score of 40 is assigned for a gait velocity of 91 to 1.0 m/s; and a score of 50 is assigned for a gait velocity greater than 1.1 to 1.2 m/s and above. For posture deviation, a score of 15 is assigned to a posture deviation/sway from midline of 11 to 16 degrees or more; a score of 30 is assigned to a posture deviation/sway from midline of 6 to 10 degrees; a score of 40 is assigned to a posture deviation/sway of 2 to 5 degrees; and a score of 50 is assigned to a posture deviation/sway of 0 to 1 degrees. The two scores are added to provide the FPs which is interpreted as 0-30=very high risk of fall; 31-49=moderate risk of fall; 50-70=low risk of fall; 71-90=very low risk of fall; and 91-100=negligible risk of fall.

In the systems and methods, one or more (or even all) of the measurements used to generate the metrics described above can be made using the sensor unit 358 (FIG. 3) and its associated sensors 304. For example, an accelerometer in the sensor unit 358 can be used to measure step count, step velocity, gait velocity, step distance, time to walk, posture, sagittal balance/posture, coronal balance/posture, fall prediction, or the like or any combination thereof. A gyroscope in the sensor unit 358 can be used to measure posture, sagittal balance/posture, coronal balance/posture, fall prediction, or the like or any combination thereof. The sensor unit can include one or more other sensors such as, for example, a heart rate sensor (to measure heart rate or sleep cycle) or a temperature sensor. In at least some embodiments, the sensor unit 358 may include a smoke or nicotine sensor to determine if the user smokes (and, optionally, how much) or if the user is exposed to substantial second-hand smoke.

A patient device 106 (FIG. 1) or a clinician device 108 (or both) can include an application that communicates with the sensor unit 358 (FIG. 3) through a wired or wireless connection. The sensor unit 358 may collect or determine measurements such as, for example, which may include; number of steps, gait velocity (speed), gait distance, sagittal posture, coronal posture, fall prediction, or the like or any combination thereof and may communicate those measurements to the patient device 106 or clinician device 108 (or both).

The application on the patient device 106 may provide the patient with information regarding the measurements (for example, lists of the measurements, graphs of the measurements, averages or daily numbers for the measurements or the like or any combination thereof), as well as any of the metrics described above (including for example, graphs or lists associated with the metric). The application may permit the patient to view, and update the progress of their rehabilitation or their physical therapy or exercises. The application may allow the patient access to some or all profile details and may permit access to sensor unit set-up and calibration applications or protocols.

The application on the clinician device 108 may allow the clinician to connect to the sensor unit during an office visit such as, for example, before or after the diagnosis, rehabilitation treatment or surgical intervention has taken place. The clinician device 108 may allow the clinician to monitor the patient recovery. The clinician device may allow a clinician to conduct in-office measurements that can be used to generate any of the metrics, such as the GPi.

Another application that may be provided on a clinician device 108 or other device can include an account manager, patient profile manager, or the like. This application may also allow management of settings for the applications on the patient or clinician device.

FIGS. 4-12 illustrate screenshots or interfaces of one embodiment of an application or user interface for the patient device or clinician device. The illustrated user application interface is particularly useful for a mobile device such as a smartphone or tablet, but can also be used with other devices such as desktop or laptop computers.

FIG. 4 illustrates one embodiment of a user interface 460 in which the current values of measurements are presented at, for example, region 462. The user interface also presents one or more determined metrics, such as the GPi, in region 464. In region 466, a graph of one or more measurements is presented and may include information about the measurements over time. In FIG. 4, the graph is of sagittal and coronal posture for a day (or other period of time) indicating by color, intensity, or the like the frequency of that measurement over the period of time. This particular graph also includes indications of possible conditions (for example, kyphosis or lordosis) based on the measurements.

Figure 6:
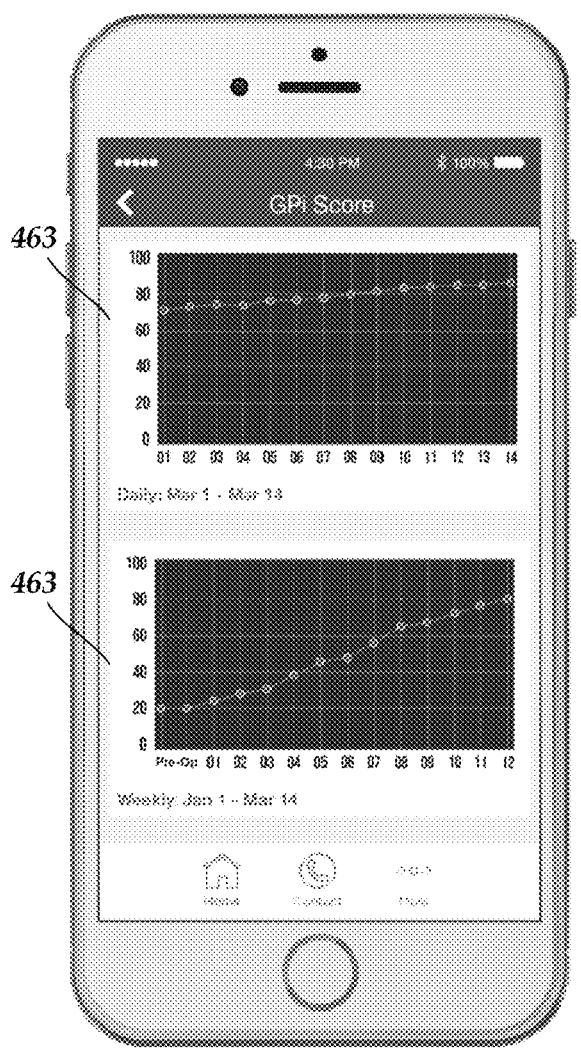
FIG. 6 is a diagram of one embodiment of a user interface for a mobile device to display a summary of repetitions of exercises, according to the invention.
Figure 7:
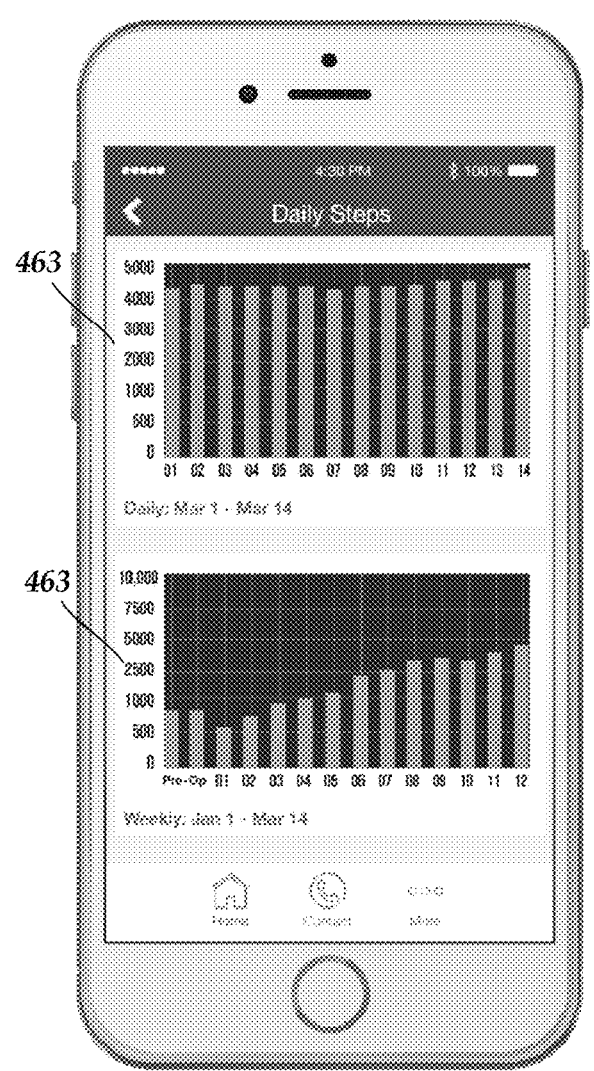
FIG. 7 is a diagram of one embodiment of a user interface for a mobile device to display information obtained from a sensor unit, according to the invention.
Figures 8, 9:
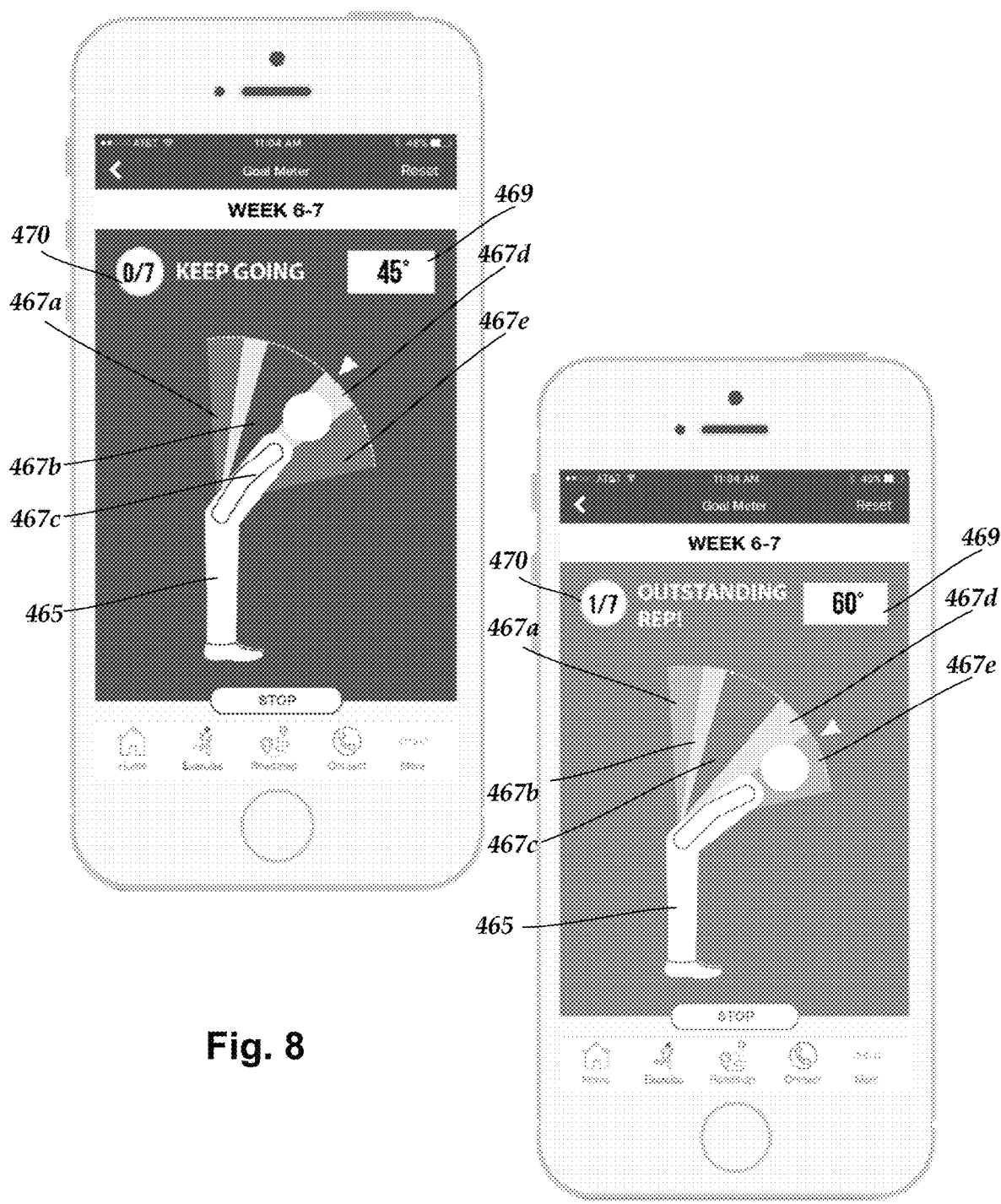
FIG. 8 is a diagram of another embodiment of a user interface to display information obtained from a sensor unit, according to the invention.
FIG. 9 is a diagram of a further embodiment of a user interface to display information obtained from a sensor unit, according to the invention.
Figure 10:
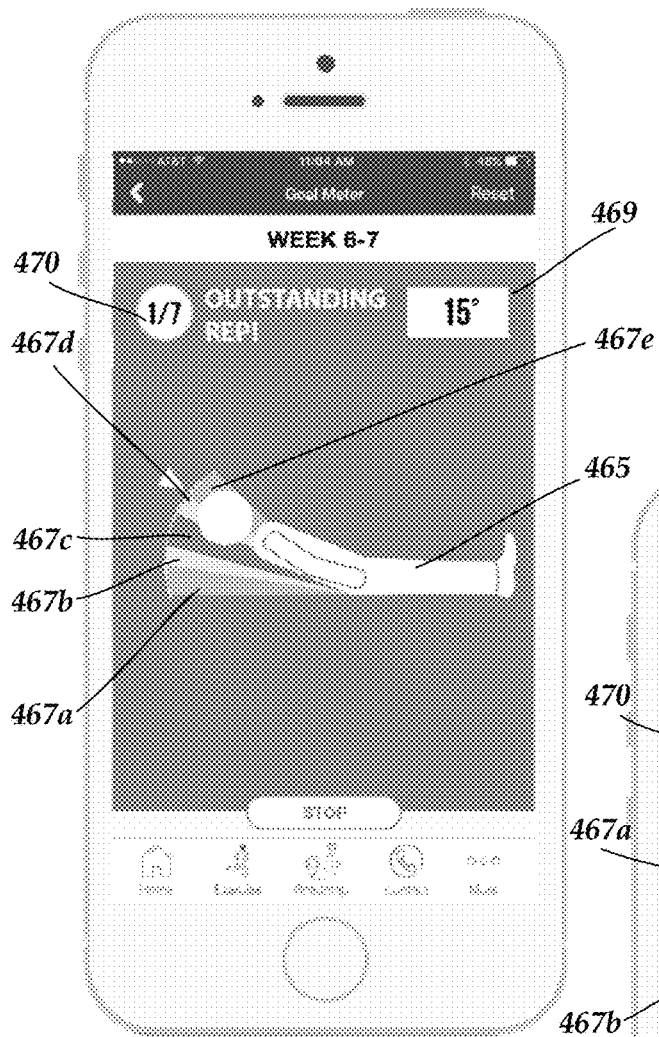
FIG. 10 is a diagram of yet another embodiment of a user interface to display information obtained from a sensor unit, according to the invention.
Figure 11:
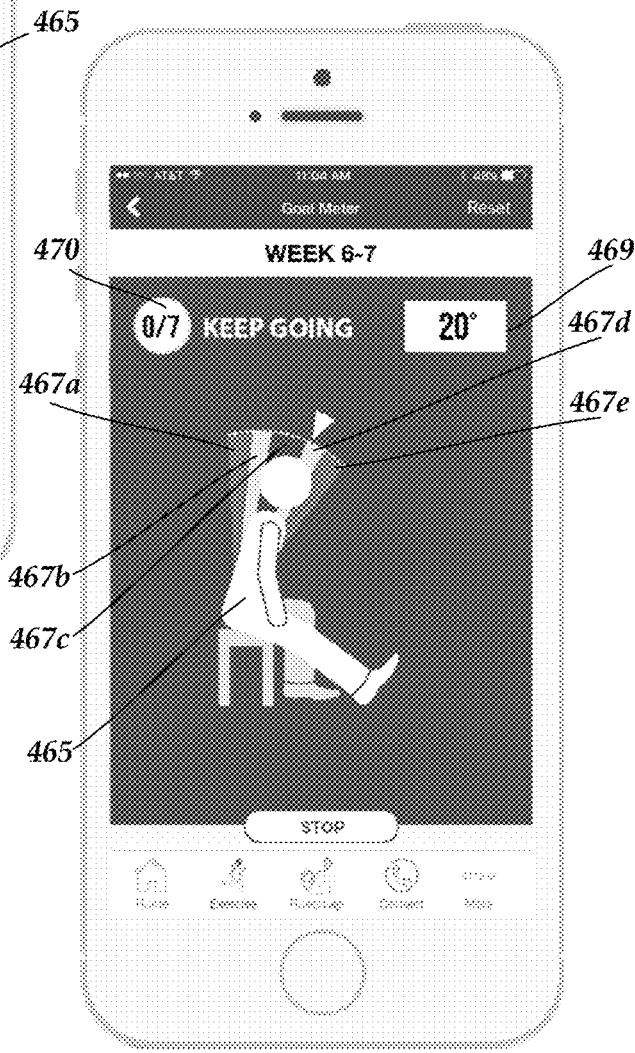
FIG. 11 is a diagram of another embodiment of a user interface to display information obtained from a sensor unit, according to the invention.
Figure 12:
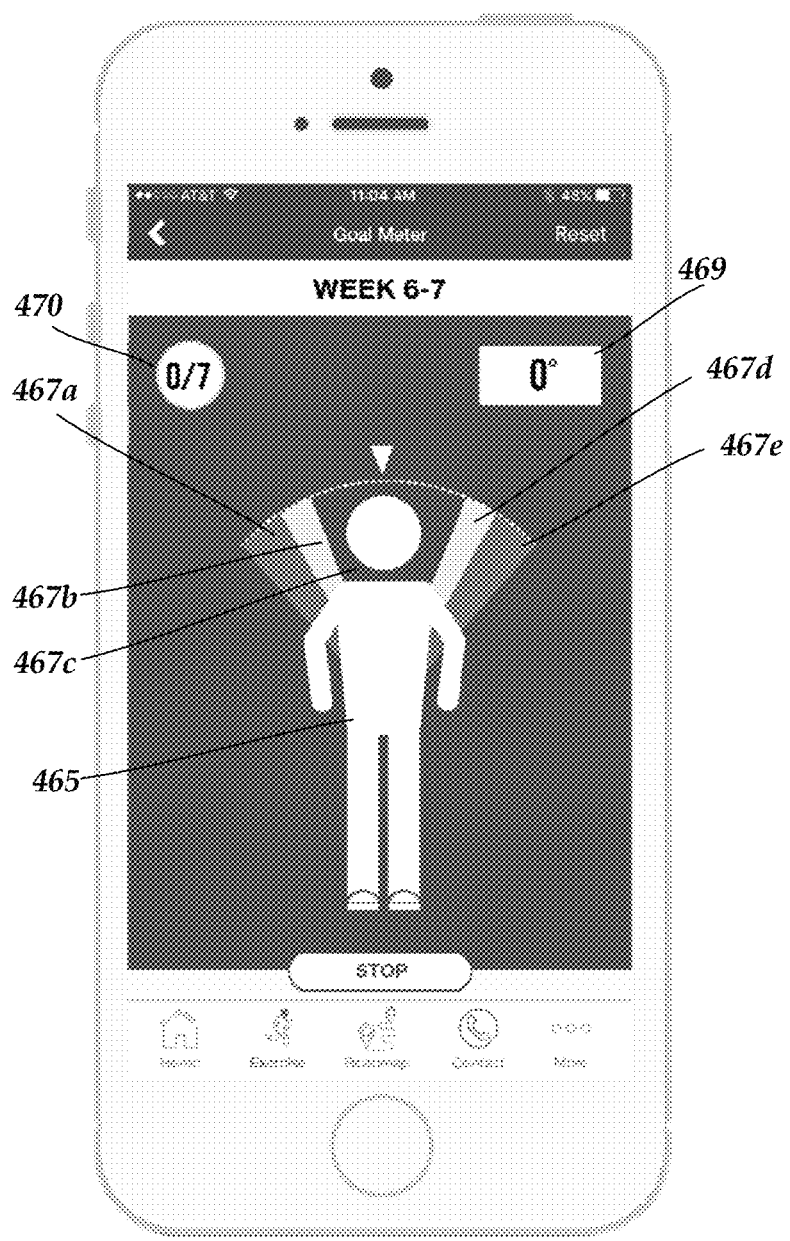
FIG. 12 is a diagram of a further embodiment of a user interface to display information obtained from a sensor unit, according to the invention.

FIGS. 5-7 illustrates graphs 463 of measurements (FIGS. 5 and 7) or metrics (FIG. 6) over a period of time (for example, weekly or daily). In the illustrated embodiments, graphs of coronal and sagittal posture are made with each point corresponding to a weekly measurement (or average of measurements over a week). This permits the user (e.g., patient or clinician) to monitor changes (e.g., improvements or degradation) over time.

FIGS. 8-12 graphically illustrate movement goals for exercises, range of motion measurements, or posture evaluations. In each of these Figures, a human icon 465 is presented and can be adjusted, based on the measurements of the sensor unit, to represent the current motion, position, or posture of the user. In addition, range increments 467a, 467b, 467c, 467d, 467e are presented for exercise or range of motion measurements. In some embodiments, the range increments 467a, 467b in at least FIGS. 8 and 9 may also be presented for posture evaluations. The current position 469 can be presented, as well as the number of exercise repetitions 470. The range increments 467a, 467b, 467c, 467d, 467e may have different colors to represent approaching a goal (e.g., range increments 467b, 467d) or achieving a goal (e.g., range increments 467a, 467e). These may be associated with colors in the range increments or on the background of the interface or associated with encouraging messages to "Keep Going" or to acknowledge an "Outstanding Rep!" or other messages.

The methods and systems described herein may be embodied in many different forms and should not be construed as limited to the embodiments set forth herein. Accordingly, the methods and systems described herein may take the form of an entirely hardware embodiment, an entirely software embodiment or an embodiment combining software and hardware aspects. Systems referenced herein typically include memory and typically include methods for communication with other devices including mobile devices. Methods of communication can include both wired and wireless (e.g., RF, optical, or infrared) communications methods and such methods provide another type of computer readable media; namely communication media. Wired communication can include communication over a twisted pair, coaxial cable, fiber optics, wave guides, or the like, or any combination thereof. Wireless communication can include RF, infrared, acoustic, near field communication, Bluetooth™, or the like, or any combination thereof.

It will be understood that each block of the flowchart illustrations, and combinations of blocks in the flowchart illustrations and methods disclosed herein, can be implemented by computer program instructions. These program instructions may be provided to a processor to produce a machine, such that the instructions, which execute on the processor, create means for implementing the actions specified in the flowchart block or blocks disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computer.

The above specification provides a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. A system for monitoring a user, the system comprising:
at least one processor programmed to perform actions comprising:
receiving movement data from a device measuring movement of the user;
determining a step count from the movement data;
determining a gait velocity from the movement data;
determining a step distance from the movement data;
determining a posture of the user from the movement data;
determining a gait posture index as a function of the step count, the gait velocity, the step distance, and the posture; and
performing an action selected from providing a warning to the user or a clinician when the gait posture index meets a threshold criterion; altering a treatment, a physical therapy regimen, or an exercise regimen based on the gait posture index; recommending the alteration of the treatment, the physical therapy regimen, or the exercise regimen based on the gait posture index; or providing a preliminary or a final diagnosis based on the gait posture index.

2. The system of claim 1, further comprising the device, wherein the device comprises at least an accelerometer to produce the movement data.

3. The system of claim 2, wherein the device comprises a sensor unit configured to be disposed on the user, wherein the sensor unit comprises at least one of the at least one processor.

4. The system of claim 3, further comprising a patient device comprising a display and a communication arrangement configured for communication with the sensor unit, wherein the sensor unit comprises a communication unit for communication with the patient device.

5. The system of claim 3, further comprising a clinician device comprising a display and a communication arrangement configured for communication with the sensor unit, wherein the sensor unit comprises a communication unit for communication with the clinician device.

6. The system of claim 1, further comprising a patient device comprising a display and the at least one processor, wherein the actions further comprise displaying the gait posture index on the display of the patient device.

7. The system of claim 1, wherein determining the gait posture index comprises determining a score for each of the step count, the gait velocity, the step distance, and the posture and combining the scores to obtain the gait posture index.

8. The system of claim 7, wherein combining the scores comprises weighting the scores and adding the weighted scores together to determine the gait posture index.

9. The system of claim 7, wherein determining the score comprises determining the score for a one of the step count, the gait velocity, the step distance, or the posture by determining a position of the one of the step count, the gait velocity, the step distance, or the posture between a minimum value and a maximum value for the one of the step count, the gait velocity, the step distance, or the posture.

10. A system for monitoring a user, the system comprising:
at least one processor programmed to perform actions comprising:

receiving movement data from a device measuring movement of the user;

determining a gait velocity from the movement data;

determining a posture deviation from the movement data; and determining a fall prediction score as a function of the gait velocity and the posture deviation by determining a score for each of the gait velocity and the posture deviation using the movement data and combining the scores to obtain the fall prediction score; and performing an action selected from providing a warning to the user or a clinician when the fall prediction score meets a threshold criterion; altering a treatment, a physical therapy regimen, or an exercise regimen based on the fall prediction score; recommending the alteration of the treatment, the physical therapy regimen, or the exercise regimen based on the fall prediction score; or providing a preliminary or a final diagnosis based on the fall prediction score.

11. The system of claim 10, further comprising the device, wherein the device comprises at least an accelerometer to produce the movement data.

12. The system of claim 11, wherein the device comprises a sensor unit configured to be disposed on the user, wherein the sensor unit comprises at least one of the at least one processor.

13. The system of claim 12, further comprising a patient device comprising a display and a communication unit configured for communication with the sensor unit, wherein the sensor unit comprises a communication arrangement for communication with the patient device.

14. The system of claim 12, further comprising a clinician device comprising a display and a communication arrangement configured for communication with the sensor unit, wherein the sensor unit comprises a communication unit for communication with the clinician device.

15. The system of claim 10, further comprising a patient device comprising a display and the at least one processor, wherein the actions further comprise displaying the fall prediction score on the display of the patient device.

16. The system of claim 10, wherein combining the scores comprises weighting the scores for the gait velocity and the posture deviation and adding the weighted scores together to determine the fall prediction score.

17. A system for monitoring a user, the system comprising:

at least one processor programmed to perform actions comprising:

receiving movement data from a device measuring movement of the user;

determining a gait velocity from the movement data;

determining a posture deviation from the movement data; and determining a fall prediction score as a function of the gait velocity and the posture deviation; and performing an action selected from providing a warning to the user or a clinician when the fall prediction score meets a threshold criterion; altering a treatment, a physical therapy regimen, or an exercise regimen based on the fall prediction score; recommending the alteration of the treatment, the physical therapy regimen, or the exercise regimen based on the fall prediction score; or providing a preliminary or a final diagnosis based on the fall prediction score.

18. The system of claim 17, further comprising the device, wherein the device comprises at least an accelerometer to produce the movement data.

19. The system of claim 17, wherein the device further comprises a gyroscope to produce the movement data.

20. The system of claim 17, further comprising a sensor unit configured to be disposed on the user and a patient device comprising a display and a communication arrangement configured for communication with the sensor unit, wherein the sensor unit comprises at least one of the at least one processor and a communication unit for communication with the patient device.

* * * * *